United States Patent
Nemoto

[11] Patent Number: 6,039,925
[45] Date of Patent: Mar. 21, 2000

[54] FLUORESCENCE DETECTOR

[75] Inventor: Ryoji Nemoto, Honjo, Japan

[73] Assignee: Hitachi Electronics Engineering Co., Ltd., Tokyo, Japan

[21] Appl. No.: 09/123,481

[22] Filed: Jul. 28, 1998

[30] Foreign Application Priority Data

Aug. 7, 1997 [JP] Japan .................................... 9-225696

[51] Int. Cl.[7] .................................................. G01N 21/64
[52] U.S. Cl. ...................... 422/82.08; 204/603; 356/344; 250/458.1
[58] Field of Search .......................... 422/82.08; 436/172, 436/94; 204/603, 452; 356/344; 250/458.1

[56] References Cited

U.S. PATENT DOCUMENTS

| | | |
|---|---|---|
| 5,162,654 | 11/1992 | Kostichka et al. . |
| 5,277,780 | 1/1994 | Kambara . |
| 5,534,703 | 7/1996 | Kambara et al. ..................... 250/458.1 |
| 5,584,982 | 12/1996 | Dovichi et al. .......................... 204/603 |
| 5,694,215 | 12/1997 | Carver ..................................... 356/246 |
| 5,699,157 | 12/1997 | Parce ...................................... 356/344 |
| 5,710,628 | 1/1998 | Waterhouse et al. ................... 356/344 |

FOREIGN PATENT DOCUMENTS

| | | |
|---|---|---|
| 0 454 286 | 10/1991 | European Pat. Off. . |
| 0 724 153 | 7/1996 | European Pat. Off. . |
| 5-72177 | 3/1993 | Japan . |
| WO96/23213 | 8/1996 | WIPO . |

OTHER PUBLICATIONS

Analytical Chemistry, vol. 66, No. 7, Apr. 1, 1994, "Multiple Sheath–Flow Gel Capillary–Array Electrophoresis for Multicolor Fluorescent DNA Detection" S. Takahashi et al, pp. 1021–1026.

*Primary Examiner*—Jeffrey Snay
*Attorney, Agent, or Firm*—Beall Law Offices

[57] ABSTRACT

The improved fluorescence detector comprises a tubular electrophoretic device through which a sample labelled with four kinds of fluorescent dye is caused to migrate, illumination optics for illuminating the tubular electrophoretic device with exciting light and detection optics for detecting the fluorescence emitted from the sample illuminated with the exciting light and it is characterized in that a plurality of tubular electrophoretic devices (1) are arranged in a row, a plurality of graded-index lenses (9) are arranged parallel to and in the same number as said plurality of tubular electrophoretic devices (1), each lens array being composed of four vertically stacked graded-index lenses, a plurality of bandpass filter arrays (11) are also arranged parallel to and in the same number as said plurality of electrophoretic devices (1), each filter array being composed of four filters arranged vertically in a row, and a light-receiving element of a planar type (13) is provided at the back of the rows of said bandpass filters (11). The apparatus is an efficient and compact multicolor fluorescence detector capable of real-time detection.

6 Claims, 1 Drawing Sheet

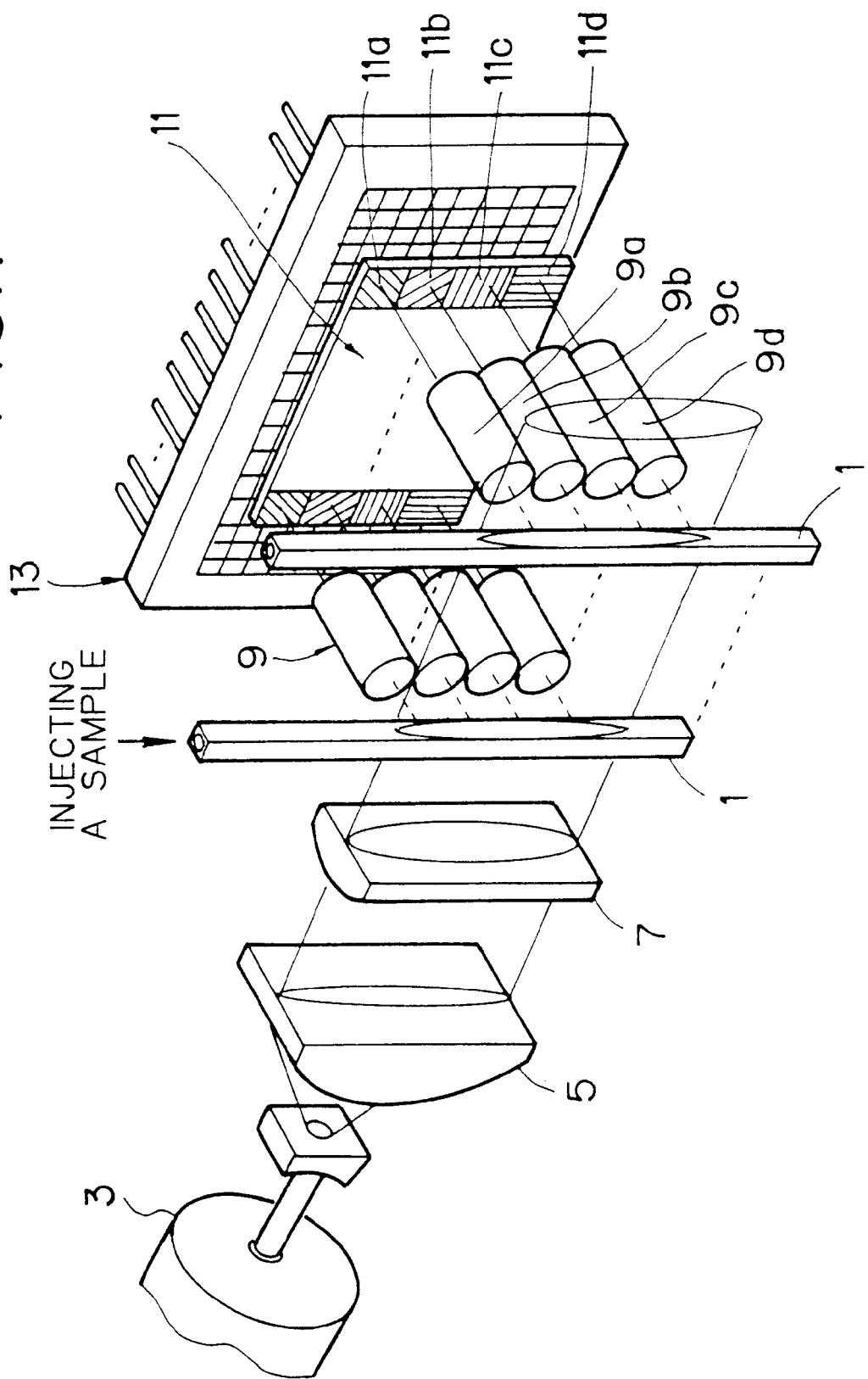

FLUORESCENCE DETECTOR

BACKGROUND OF THE INVENTION

This invention relates to a multi-color fluorescence detector, more particularly to a gel electrophoretic apparatus for electrophrescing the four constituent bases of DNA labelled with a corresponding number of fluorescent dyes.

Gel electrophoresis is practiced extensively as a technique for determining the base sequences of DNA and other proteins. Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects the fluorescence emitted upon irradiation with light is being reviewed.

In this method, fluorophore-labelled DNA fragments are caused to migrate through a gel and a light excitation portion and a photodetector are provided for each electrophoresis track in an area 15–20 cm below the start point of electrophoresis. The DNA fragments are assayed as they pass through the line connecting the light excitation portion and the photodetector. A typical procedure of the method is described below. First, using as a template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster will it move and vice versa. This is the principle behind the fractionation of DNA by molecular weight.

The fluorescent dyes currently used for DNA labelling in base sequence determination include fluorescein isothiocyanate (FITC), eosin isothiocyanate (EITC), tetramethylrhodamine isothiocyanate (TMRITC) and substituted rhodamine isothiocyanate (XRITC). Instead of labeling the sample with one fluorescent dye, it may be labelled with two fluorescent dyes such that the fluorescence emitting at two different wavelengths is measured and this contributes to a higher throughput in analysis.

Consider, for example, the case of labelling DNA fragments with FITC and XRITC. Upon illumination with laser light, the dyes emit fluorescence at wavelengths of about 520 nm and 604 nm. When two fluorescent dyes are used, the number of samples that can be analyzed per gel electrolyte is of course doubled but, what is more, the base length that can be identified is increased as compared with the case of using only one dye. The number of lanes that are produced from one sample is four and this is invariable whether one or two dyes are used. On the other hand, the number of samples that can be analyzed per gel electrolyte which is eight in the case of using one fluorescent dye is doubled to 16 when two dyes are used. The base length that can be identified is increased from 400 bp to 450 bp.

To further enhance the throughput of analysis, a multi-color DNA sequencer is being developed in which the four DNA bases are labelled with four fluorescent dyes that emit at different wavelengths. In one type of the multi-color DNA sequencer, a plurality of bandpass filters on a rotating disk are alternately inserted into the optical path of detecting light so as to detect the fluorescence issuing from the sample. However, the need to switch between filters at given time intervals makes it impossible to perform real-time detection. Furthermore, the installation of the rotating mechanism increases not only the complexity but also the overall size of the analyzer. In another type of the multi-color DNA sequencer, a dispersing prism is inserted into the fluorescence detecting optics to separate the light from the sample into different wavelength components. The light from the sample is collected with a condenser lens, made parallel with a collimator and separated into spectral components which are respectively condensed on associated sensors. However, this approach involves mechanistic difficulties due to the need for correcting aberrations such as chromatic aberration and the prism-induced aberration.

SUMMARY OF THE INVENTION

The present invention has been accomplished under these circumstances and has as an object providing an efficient and compact multi-color fluorescence detector capable of real-time detection.

This object of the invention can be attained by a fluorescence detector comprising a tubular electrophoretic means through which a sample labelled with four kinds of fluorescent dye is caused to migrate, illumination optics for illuminating the tubular electrophoretic means with exciting light and detection optics for detecting the fluorescence emitted from the sample illuminated with the exciting light, characterized in that a plurality of the tubular electrophoretic means are arranged in a row, a plurality of graded-index lens arrays are arranged parallel to and in the same number as said plurality of tubular electrophoretic means, each lens array being composed of four vertically stacked graded-index lenses, a plurality of bandpass filter arrays are also arranged parallel to and in the same number as said plurality of electrophoretic means, each filter array being composed of four filters arranged vertically in a row, and a light-receiving means of a planar type is provided at the back of the rows of said bandpass filters.

BRIEF DESCRIPTION OF THE DRAWING

FIG. 1 is a diagrammatic perspective view showing an exemplary layout of the multi-color fluorescence detector of the invention.

THE PREFERRED EMBODIMENTS OF THE INVENTION

FIG. 1 is a diagrammatic perspective view showing an exemplary layout of the multi-color fluorescence detector of the invention. The apparatus uses a hollow glass tube 1 (i.e. <100 μm) as a tubular electrophoretic means and in the illustrated case it has a rectangular cross section. The hollow space of the glass tube 1 is filled with a polyacrylamide gel or any other polymer that is suitable as a migration medium. A sample having the four DNA bases labelled with four fluorescent dyes is injected into the glass tube and allowed to migrate. The glass tube may have a circular rather than rectangular cross section.

When the sample has migrated down through the glass tube over a specified distance, say, 30–40 cm, laser light for fluorescence excitation is applied to the sample to form a beam spot, say, 0.1–0.4 mm in diameter which is sufficiently smaller than the band width of the sample. The illumination optics comprises a laser light source 3, a collimator lens 5 and a cylindrical lens 7. The laser light source 3 is not limited to any particular type but in consideration of the fluorescence dyes to be used, it is preferred to use an argon laser having an excitation wavelength of 488 or 514.5 nm.

When irradiated with the exciting light from the illumination optics, the fluorophore-labelled sample migrating along the gel electrolyte layer in the glass tube 1 emits fluorescence, which is accepted as parallel light into the detection optics by means of four graded-index lenses 9a–9d each being so set as to have a focal position at the center through the glass tube 1.

Each of the graded-index lenses 9 used in the invention is also known as a "Selfoc lens" which is a cylindrical lens having a refractive index distribution in the radial direction. The graded-index lens array is in close proximity with the electrophoresis plate for imaging the fluorescent image and this insures uniform signal levels to be attained between the center and either end of the plate. As a result, the uniformity of S/N ratio is improved and one can read the length of bases in lanes in the marginal portions of the plate as precisely as in lanes at the center and nearby areas. Since the graded-index lenses are disposed in an array, adjacent lens images will overlap, whereby 1:1 erecting imaging optics is provided in the lens mounting area. The "Selfoc lens" to be used in the invention is commercially available under code number SLA-20B (FO. 96) and has a diameter of about 1 mm with a length of about 12–13 mm. Needless to say, the lenses 9 are supported in a suitable enclosure or holder to make an array configuration. In the present invention, the Selfoc lenses may be replaced by a camera lens commonly employed with the DNA sequencer.

The detection optics has in its optical path four bandpass filters ($Bp_1$–$Bp_4$) 11a, 11b, 11c and 11d that transmit light at wavelengths near the peak wavelengths from the respective fluorescent dyes and which are arranged integrally in a plane normal to the optical axis. The parallel light accepted into the detection optics is separated by these filters 11a–11d into spectral components within four areas in the plane normal to the optical axis. The four bandpass filters ($Bp_1$–$BP_2$) 11a, 11b, 11c and 11d correspond to the Selfoc lenses 9a–9d, respectively, which are stacked vertically. The bandpass filters are not limited to any particular size but those about 150 µm×150 µm in size are generally preferred.

The fluorescence passing through each of the bandpass filters is picked up by a two-dimensional CCD array 13 placed at the back of the filter assembly. To identify colors and electrophoretic lanes, the pixel numbers from the CCD array 13 may be counted. The subsequent processing for identifying the DNA bases may be performed on a conventional type of multi-color resolving software.

For the sake of convenience in explanation, FIG. 1 shows only one glass tube 1 at each end of the apparatus but in practice, more than one, say, 40–100, glass tubes may be used. In FIG. 1, the illumination optics is arranged in such a way that it is perpendicular to the detection optics with respect to the glass tube but this is not the sole case of the invention and the two optics may be arranged in a face-to-face relationship with respect to the glass tube. In FIG. 1, the exciting light is launched into the glass tube 1 in a direction normal to the side of each graded-index lens 9 and parallel to the bandpass filters 11. In a different embodiment, the exciting light may be launched in a direction normal to both an end face of each graded-index lens 9 and the bandpass filter array. Although not shown, the top of the glass tube 1 is immersed in a buffer solution in an upper buffer tank whereas the bottom of the glass tube is immersed in a buffer solution in a lower buffer tank. The upper buffer tank is connected to a top electrode whereas the lower buffer tank is connected to a bottom electrode so that electrophoresis of the sample is effected with a voltage applied between the two electrodes. An example of the gel electrophorescing apparatus using more than one glass tube is disclosed in Japanese Laid-Open Patent Application (kokai) No. 72177/1993, which is incorporated herein by reference.

As described on the foregoing pages, the fluorescence detector of the present invention enables each of the sensors to perform real-time detection, thereby achieving an improvement in sensitivity. What is more, the elimination of mechanical drives not only contributes to a reduction in the overall size of the apparatus but also enables simultaneous detection of more than one lane.

What is claimed is:

1. A fluorescence detector comprising a tubular electrophoretic means through which a sample labelled with four kinds of fluorescent dye is caused to migrate, illumination optics for illuminating the tubular electrophoretic means with exciting light and detection optics for detecting the fluorescence emitted from the sample illuminated with the exciting light, wherein a plurality of tubular electrophoretic means are arranged in a row, a plurality of graded-index lens arrays are arranged parallel to and in the same number as said plurality of tubular electrophoretic means, each lens array being composed of four vertically stacked graded-index lenses, a plurality of bandpass filter arrays are also arranged parallel to and in the same number as said plurality of electrophoretic means, each filter array being composed of four filters arranged vertically in a row, and a planar light-receiving means is provided at the back of the rows of said bandpass filters.

2. The fluorescence detector according to claim 1, wherein said tubular electrophoretic means is a glass tube, said graded-index lenses are Selfoc lenses, and said light-receiving means is a two-dimensional CCD array.

3. The fluorescence detector according to claim 2, wherein said tubular electrophoretic means is a hollow glass tube having a rectangular cross section, with its hollow space being filled with a migration medium.

4. The fluorescence detector according to claim 1, wherein said illumination optics for illuminating said tubular electrophoretic means with exciting light comprises at least a laser light source a collimator lens and a cylindrical lens.

5. The fluorescence detector according to claim 4, comprising a gel electrophoretic apparatus for electrophorescing DNA bases labelled with a plurality of fluorescent dyes.

6. The fluorescence detector according to claim 1, comprising a gel electrophoretic apparatus.

* * * * *